United States Patent
Oku et al.

(10) Patent No.: US 6,497,862 B2
(45) Date of Patent: Dec. 24, 2002

(54) COMPOSITION FOR INHIBITING BODY ODOR AND USES THEREOF

(75) Inventors: Kazuyuki Oku, Okayama (JP); Michio Kubota, Okayama (JP); Shigeharu Fukuda, Okayama (JP); Toshio Miyake, Okayama (JP)

(73) Assignees: Kabushiki Kaisha Hayashibara, Okayama (JP); Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 09/795,522

(22) Filed: Mar. 1, 2001

(65) Prior Publication Data

US 2001/0031249 A1 Oct. 18, 2001

(30) Foreign Application Priority Data

| Mar. 2, 2000 | (JP) | 2000-058032 |
| May 29, 2000 | (JP) | 2000-159204 |
| Jul. 4, 2000 | (JP) | 2000-202972 |
| Sep. 5, 2000 | (JP) | 2000-269165 |

(51) Int. Cl.$^7$ ............................................. A61K 7/32
(52) U.S. Cl. .................. 424/65; 424/401; 424/443; 424/445; 424/447
(58) Field of Search .................. 424/401, 65, 443, 424/445, 447

(56) References Cited

U.S. PATENT DOCUMENTS

| 3,741,776 A | 6/1973 | Mitsuhashi et al. |
| 4,408,041 A | 10/1983 | Hirao et al. |
| 6,224,888 B1 * | 5/2001 | Vatter et al. ................ 424/401 |

FOREIGN PATENT DOCUMENTS

| EP | 0 606 753 | 7/1994 |
| EP | 0 628 630 | 12/1994 |
| EP | 0 636 693 | 2/1995 |
| EP | 0 671 470 | 9/1995 |
| EP | 0 674 005 | 9/1995 |
| EP | 0 688 866 | 12/1995 |
| EP | 0 688 867 | 12/1995 |
| EP | 0 690 130 | 1/1996 |
| EP | 0 695 804 | 2/1996 |
| EP | 0 697 461 | 2/1996 |
| EP | 0 704 531 | 4/1996 |
| EP | 0 709 461 | 4/1996 |
| JP | 47 13699 | 6/1973 |
| JP | 63 2439 | 1/1988 |
| JP | 7 143876 | 6/1995 |
| JP | 7 213283 | 8/1995 |
| JP | 7 170977 | 11/1995 |
| JP | 7 298880 | 11/1995 |
| JP | 7 322883 | 12/1995 |
| JP | 8 84586 | 2/1996 |
| JP | 8 66187 | 3/1996 |
| JP | 8 66188 | 3/1996 |
| JP | 8 73482 | 3/1996 |
| JP | 8 263 | 9/1996 |
| JP | 8 149980 | 11/1996 |
| JP | 8 336388 | 12/1996 |
| JP | 11 286428 | 10/1999 |

OTHER PUBLICATIONS

Shinichiro et al., "Development of the body odor–care products for senior citizens", *Fragrance Journal*, (1999), pp. 42–46.

* cited by examiner

*Primary Examiner*—Jose' G. Dees
*Assistant Examiner*—Konata M. George
(74) *Attorney, Agent, or Firm*—Browdy and Neimark, P.L.L.C.

(57) ABSTRACT

Disclosed are a composition for inhibiting body odor which comprises trehalose and/or maltitol as an effective ingredient, a method for inhibiting body odor by using the composition, and an article incorporated with the composition.

18 Claims, 1 Drawing Sheet

COMPOSITION FOR INHIBITING BODY ODOR AND USES THEREOF

BACKGROUND OF THE INVENTION

1. Field of the Invention

Figure 1:
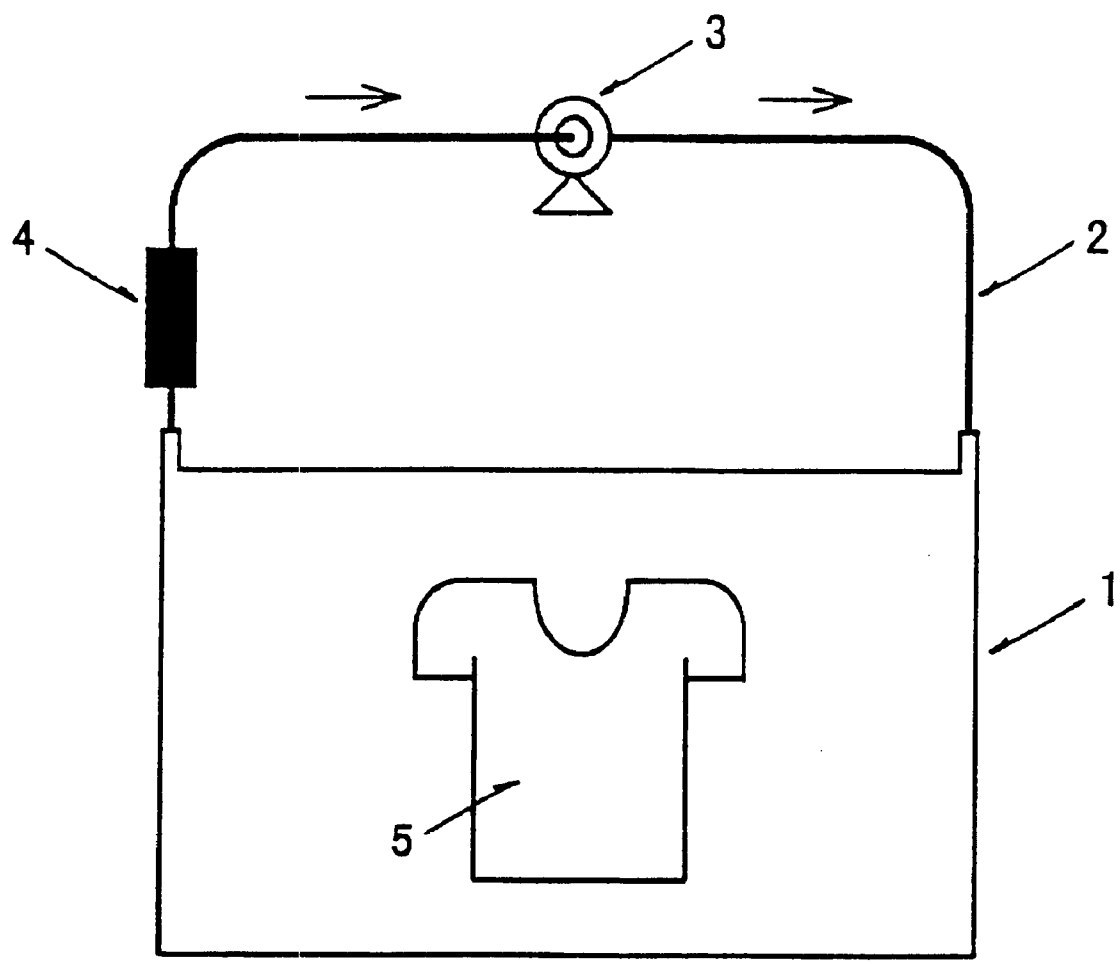

The present invention relates to a novel composition for inhibiting body odor, and more particularly, to a composition for inhibiting body odor which comprises trehalose and/or maltitol as an effective ingredient, and uses thereof.

2. Description of the Prior Art

As an increased concerning on deodorization of body odor such as smell of sweat, breath odor, and armpit odor, the demand for etiquette products for inhibiting body odor is being increased in these days. It has been revealed that the formation of body odor is influenced by diseases, body conditions, genetic constitutions, and lifestyles such as meals, smoking, and frequency of bathing. The research for substances causative of body odor has been proceeded recently and confirmed that volatile aldehydes, formed from higher fatty-acids secreted from living bodies and ester derivatives thereof, are the main substances causative of body odor. In addition to the above body odor, it is being pointed out the existence of body odor specific to middle and senior generations, i.e., ageing odor, induced by ageing. For example, in "Fragrance Journal", pp. 42–46, September, 1999, and Japanese Patent Kokai No. 286,428/99, a body odor specific to these generations is named "KAREI-SHU" (throughout the specification, the specific body-odor of the middle and senior generations is referred to as "KAREI-SHU" hereinafter) and the formation of "KAREI-SHU" deeply relates to substances having unsaturated groups such as 2-nonenal and 2-octenal, as a kind of volatile aldehyde, formed from 9-hexadecenoic acid which is found in an increased amount in the sebum of human middle and senior generations. In addition to the above body-odor, the demand for deodorization of body odor of animals such as pets and livestocks are also increased similarly as in humans, and the measure thereof has been being researched.

As a result, at present, the measure for human and animal body-odor has been practiced from various aspects. Theoretical classification thereof is as follows: (1) Masking body-odor using a flavor ingredient, (2) physically absorbing ingredients of body odor or the precursors thereof to inhibit the dispersion of the ingredients, and (3) inhibiting the formation per se of the ingredients of body odor from precursors thereof.

The method (1) could not be a substantial solution because it does not inhibit the formation of body odor per se and may form a new odor, which is not necessarily be a satisfactory smell, due to the coexistence of the problematic body-odor and the flavor ingredient. Representative examples of the method (2) are, for example, a method for inhibiting the dispersion of ingredients of body odor by using the inclusion- and absorption-abilities of cyclodextrins, activated charcoals, etc. The method using cyclodextrins could not be a substantial solution because the ingredients of body odor, once included by cyclodextrins, may be re-released by the coexisting other substances, while the method using activated charcoals could not necessarily be effective because it could hardly exert a desired instant effect and has a limitation of direct application to living bodies. Representative examples of the method (3) include those which use antioxidants and antibacterial substances. Although the method (3) effectively inhibits the formation of body odor, the antioxidants and antibacterial substances used therein in an amount sufficient to inhibit the formation of body odor may induce, for example, undesirable results on subject's health such as stimulations and allergies to the skin of living bodies, when directly applied to the living bodies.

SUMMARY OF THE INVENTION

In view of the foregoing, the object of the present invention is to provide a means for effectively inhibiting body-odor at the formation stage of body odor and being used without less fear of affecting subject's heath.

The present inventors started to study with the aim of establishing a means for solving the above object by using the saccharides and their related substances with revealed safety of application to humans and animals. They focused on the inhibitory effect of trehalose and maltitol on the formation of volatile aldehydes and the decomposition of fatty acids and continued studying the influence of the saccharides on the formation of volatile aldehydes known as the substances causative of body odor. As a result, the present inventors found that trehalose and maltitol particularly remarkably inhibit the formation of the substances causative of body odor including 2-nonenal in a system of acceleration test under heating conditions. They also confirmed that these saccharides also exert such an effect in a test system under the temperature conditions similarly as in human body. Based on a test using volunteers, the present inventors also found that trehalose and maltitol effectively inhibit the formation of substances causative of body odor including 2-nonenal from living human bodies. The present invention was made based on these findings.

The present invention solves the above object by a composition for inhibiting body odor (called "a body-odor inhibitory agent, hereinafter") comprising trehalose and/or maltitol as an effective ingredient, a method for inhibiting body-odor using the agent, and an article incorporated with the agent.

BRIEF DESCRIPTION OF THE ACCOMPANYING DRAWING

FIG. 1 is a schematic illustration of entrapping volatile aldehydes contained in an underwear worn by a volunteer. An arrow (→) indicates a gas flow. In FIG. 1, 1 means a sealed vessel; 2, a pipe; 3, an air pump; 4, an entrapping cartridge for volatile aldehydes; and 5, an underwear after wearing.

DETAILED DESCRIPTION OF THE INVENTION

The present invention, which was made based on the fact that trehalose and maltitol effectively inhibit the formation of body odor of humans and animals including mammals, poultry, and fishery in their formation stages, provides a body-odor inhibitory agent comprising trehalose and/or maltitol as an effective ingredient and uses thereof. The term trehalose as referred to in the present invention means a disaccharide composed of two glucose molecules bound together at their reducing groups via the α,α-bond. The purity, existing form, property, and preparation method of the trehalose used in the present invention should not be restricted to a specific one as long as it can inhibit the formation of body odor of humans and animals.

The trehalose used in the present invention can be prepared by different methods. With an economical viewpoint, preferable methods are those which comprise a step of contacting with partial starch hydrolysates non-reducing saccharide-forming enzymes and trehalose-releasing enzymes as disclosed in Japanese Patent Kokai Nos. 143,876/95, 213,283/95, 322,883/95, 298,880/95, 66,187/96, 66,188/96, 336,388/96, and 84,586/96. These methods can produce trehalose in a satisfactorily-high yield from starches as relatively-low cost materials. Examples of commercially available products prepared by these methods are "TREHALOSE FOR COSMETIC USE", a crystalline trehalose hydrate having a trehalose content of 99% (w/w) or higher, commercialized by Hayashibara Shoji Inc., Okayama, Japan; "TREHA®", a crystalline trehalose hydrate having a trehalose content of 98% (w/w) or higher, commercialized by Hayashibara Shoji Inc., Okayama, Japan; and "TREHASTAR®", a trehalose high-content syrup having a trehalose content of 28% (w/w) or higher, commercialized by Hayashibara Shoji Inc., Okayama, Japan. Trehalose can be obtained by contacting maltose either with a maltose/trehalose converting enzyme as disclosed, for example, in either of Japanese Patent Kokai Nos. 170,977/95, 263/96 or 149,980/96; or with a conventionally known maltose phosphorylase or trehalose phosphorylase. Crystalline trehalose anhydride can be prepared by drying crystalline trehalose hydrate similarly as exemplified above under the normal or reduced pressure and at a temperature of 70–160° C., more preferably, under a reduced pressure and at a temperature of 80–100° C.; or by placing in a crystallizer a relatively-high trehalose content solution with a moisture content of less than 10% (w/w), stirring the solution in the presence of seed at a temperature of 50–160° C., preferably, a temperature of 80–140° C. to form a massecuite containing crystalline trehalose anhydride, and crystallizing and pulverizing the resulting massecuite by a method such as block pulverization, fluidized-bed granulation, or spray-drying. The trehalose products thus obtained can be advantageously used in the present invention.

The term maltitol as referred to in the present invention means a reduced saccharide of maltose, a disaccharide composed of two glucose molecules bound together via the α-1,4 bond. The purity, existing form, property, and preparation method of maltitol used in the present invention should not be restricted to a specific one as long as it can inhibit the formation of body odor of humans and animals. For example, the following maltitol can be advantageously used in the present invention: A maltitol syrup obtainable by the method as disclosed in Japanese Patent Kokoku No. 13,699/72 and a crystalline maltitol anhydride obtainable by the method as disclosed in Japanese Patent Kokoku No. 2,439/88, both of which were applied for by the same applicant as the present invention; and "POWDERED MABIT®", a crystalline maltitol anhydride having a maltitol content of at least 93.5% (w/w), commercialized by Hayashibara Shoji Inc., Okayama, Japan; and MABIT®", a maltitol syrup having a solid content of at least 74% by weight and a maltitol content of at least 75%, based on the weight of the dry solid (d.s.b.), commercialized by Hayashibara Shoji Inc., Okayama, Japan. When trehalose and maltitol are used together in the present invention, a mixture of trehalose and maltitol, obtained by hydrogenating a mixture of trehalose and maltose as disclosed in Japanese Patent Kokai No. 73,482/96 applied for by the same applicant as the present invention, can be arbitrarily used.

The body-odor inhibitory agent of the present invention comprises the above-mentioned trehalose and/or maltitol as an effective ingredient. The composition and property of the body-odor inhibitory agent of the present invention should not be specifically restricted as long as it comprises trehalose and/or maltitol and exerts the desired body-odor inhibitory effect in respective fields or forms to be used. The content of trehalose and/or maltitol used in the body-odor inhibitory agent of the present invention is usually about 0.001–100% (w/w), and preferably, about 0.01–50% (w/w) with respect to the total weight d.s.b., depending on the fields and forms to be used. For example, the body-odor inhibitory agent in a solution form of the present invention, which contains water and/or alcohol as a solvent, has the merit that it can be easily handled and exert a satisfactory body-odor inhibitory effect by trehalose and/or maltitol in a relatively-wide application. Examples of the alcohols usable in the present invention include lower monovalent alcohols such as ethanol, propanol, isopropanol, and butanol.

Under the limitation of not inhibiting the effect of trehalose and/or maltitol, the body-odor inhibitory agent of the present invention can be imparted with the desired properties or functions by incorporating one or more ingredients selected from saccharides other than trehalose and maltitol, humectants, antibacterial agents, bacteriostats, germicides, antiseptics, preservatives, antioxidants, ultraviolet shielding agents, ultraviolet absorbents, antiperspirants, physiological-effect-exerting ingredients, emulsifiers, surfactants, feeling improvers, powdered materials, refreshing agents, sprayings, pH-controlling agents, flavors, deodorants, colors, proteins, amino acids, fibers, lipids, salts, etc., which are used in general in respective fields where the body-odor inhibitory agent of the present invention is used.

Examples of the saccharides other than trehalose and maltitol include maltooligosaccharides such as maltose, maltotriose, and maltotetraose; cyclic saccharides such as cyclodextrins, branched cyclodextrins, and cyclodextrans; neutral saccharides such as pullulan, amylopectin, starches, soluble starches, cellulose, amylose, dextrans, curdran, laminaran, elsinan, agarose, carrageenan, mannan, inulin, levan, galactan, gum arabic, and locust bean gum. In general, these saccharides can be appropriately used depending on purposes because they can impart their inherent functions to the body-odor inhibitory agent of the present invention without deteriorating the body-odor inhibitory effect of trehalose and/or maltitol. Among the above saccharides, aqueous neutral-saccharides including pullulan can be advantageously used depending on purposes because they exert the action of protecting the skin when used by applying to the skin after incorporated into the body-odor inhibiting agent of the present invention. The content of the aforesaid ingredients in the body-odor inhibitory agent of the present invention is usually about 0.01% to about 50% (w/w) to the total weight, varying depending on the kinds of the ingredients used and the fields and forms of the body-odor inhibitory agent to be used.

The humectants usable in the present invention include the above ingredients which exert a moisture-retaining action, and others, for example, polyalcohols such as polypropylene glycol, glycerine, 1,3-butylene glycol, erythritol, dipropylene glycol, xylitol, sorbitol, and polyethylene glycol; derivatives of polysaccharides such as carboxymethyl chitin; amino acids and salts thereof such as sodium pyrrolidone carbonate; and organic acids and salts thereof such as lactic acid and sodium lactate. The content of these ingredients preferably used in the body-odor inhibitory agent of the present invention is usually about 0.1% to about 50% (w/w) to the total weight, varying depending on the kinds of the ingredients used and the fields and forms of the body-odor inhibitory agent to be used.

Examples of the antibacterial agents, bacteriostats, germicides, antiseptics, and preservatives include organic acids such as benzoic acid, sorbic acid, dehydroacetic acid, and salts thereof; esther derivatives of benzoic acid such as methyl p-hydroxybenzoate and ethyl p-hydroxybenzoate; phenols such as phenol, cresol, chlorocresol, isopropylmethylphenol, and trichlorohydroxydiphenyl ether; quaternary ammonium salts such as benzalkonium chloride, benzenethonium chloride, and cetylpyridinium chloride; chlorohexydine derivatives such as chlorohexydine gluconate, and chlorohexydine hydrochloride; diphenylurea derivatives such as trichlorocarbanide and halocarbane; and dihydropharnesol. The content of these ingredients preferably used in the body-odor inhibitory agent of the present invention is usually 0.001–5% (w/w), and preferably 0.01–1% (w/w) to the total weight, varying depending on the kinds of the ingredients used and the fields and forms of the body-odor inhibitory agent to be used.

Examples of the antioxidants usable in the present invention include, in addition to the substances having antioxidant action among the aforesaid ingredients, ascorbic acid and salts thereof, ascorbic acid derivatives such as ascorbic acid stearate and saccharide-transferred ascorbic acid, citric acid and salts thereof, tocopherol acetate, dibutylhydroxytoluene, tocopherol, palmitic acid, and salts thereof, ascorbyl palmitate, sodium pyrosulfite, butylhydroxyanisol, propyl gallate, and catechin from tea. The content of these ingredients preferably used in the body-odor inhibitory agent of the present invention is usually about 0.001% to about 10% (w/w), and preferably about 0.01% to about 5% (w/w) with respect to the total weight, varying depending on the kinds of the ingredients used and the fields and forms of the body-odor inhibitory agent used.

Examples of the ultraviolet shielding agents usable in the present invention include inorganic substances capable of shielding ultraviolet such as titanium oxide, talc, and carotenoid; and organic substances such as 5-chlorouracil, guanine and cysteine. The ultraviolet absorbents usable in the present invention include, for example, in addition to the aforesaid ingredients capable of absorbing ultraviolet, ethyl p-aminobenzoate, ethylhexyl ester p-dimethylaminobenzoate, cinoxato, 2-(2-hydroxy-5-methylphenyl)-benzotriazole, oxybenzone, urocaninc acid, and ethyl urocanate. The content of these ingredients preferably used in the body-odor inhibitory agent of the present invention is usually about 0.1 to about 50% (w/w) with respect to the total weight, varying depending on the kinds of the ingredients used and the fields and forms of the body-odor inhibitory agent used.

Examples of the antiperspirants usable in the present invention include aluminum chloride, aluminum oxychloride, basic aluminum bromide, aluminum sulfate, chlorohydroxy aluminum, chlorohydroxy aluminum zirconium, allantoin chlorohydroxy aluminum, alum, zinc sulfate, aluminum phenolsulfonate, phenolsulfonic acid, basic aluminum zinc lactate, zinc oxide, and zinc p-phenolsulfonate, as well as astringent compounds such as complexes of the above compounds and amino acids, preferably, glycine. The content of these ingredients preferably used in the body-odor inhibitory agent of the present invention is usually 0.01–40% (w/w) with respect to the total weight, varying depending on the kinds of the ingredients used and the fields and forms of the body-odor inhibitory agent used.

The ingredients, which exert pharmacological effect, usable in the present invention are preferably those which can exert anti-inflammatory action, melanin-formation inhibitory action, injury-curing promoting action, etc.; vitamins such as vitamin A including retinol; vitamin B including thiamine, pantothenic acid, and derivatives thereof; vitamin C including the aforesaid ascorbic acid and derivatives thereof; vitamin E including the aforesaid tocopherol and derivatives thereof; and vitamin P including rutin, hesperidin, naringin and derivatives thereof; hormones, particularly, such as ovarian hormone and pregnenolone; plant extracts, particularly, such as chamomile extract and licorice extract; animal extracts, particularly, such as placenta extract; and photosensitive dyes, particularly, such as photosensitizer 101 (2,2'-[3'-[2-(3-heptyl-4-methyl-4-thiazolin-2-ylidene)ethylidene]propenylene]bis(3-heptyl-4-methylthiazolium iodide, a trivial name of PLATONIN), photosensitizer 201 (3-heptyl-2-[3-heptyl-4-methyl-2(3H)-thiazolylidene)methyl]-4-methylthiazolium iodide, a trivial name of PIONIN), photosensitizer 301 (2-[2-[(5-bromo-2-pyridinyl)amino]ethenyl]-1-ethyl-6-methylpyridinium iodide, a trivial name of TAKANAL), and photosensitizer 401 (3,4-dimethyl-2-[2-(phenylamino)ethenyl]oxazolium iodide, a trivial name of LUMINEX). The content of these ingredients preferably used in the body-odor inhibitory agent of the present invention is usually 0.0001–5% (w/w) with respect to the total weight, varying depending on the kinds of the ingredients used and the fields and forms of the body-odor inhibitory agent used.

Examples of the emulsifiers and surfactants usable in the present invention include esters such as sorbitan fatty acid ester, polyoxyethylene fatty acid ester, lipophilic glyceryl monostearate, glyceryl monostearate selfemulsifying, trimethylolpropane trioctanoate, polyglyceryl fatty acid ester, sucrose fatty acid ester; ethers such as polyoxyethylene alkyl ether; and lipids such as lecithin. The content of these ingredients preferably used in the body-odor inhibitory agent of the present invention is usually 0.01–20% (w/w) with respect to the total weight, varying depending on the kinds of the ingredients used and the fields and forms of the body-odor inhibitory agent used.

Examples of the feeling improvers preferably usable in the present invention include straight and/or cyclic silicon oils having a viscosity of not higher than 100 $mm^2$/sec, represented by kinematic viscosity at 25° C.; methylcyclopolysiloxane, dimethylpolysiloxane, hexamethyldisiloxane, octamethyltrisiloxane, methylphenylpolysiloxane, and organohydrogenpolysiloxane. The content of these ingredients preferably used in the body-odor inhibitory agent of the present invention is usually 0.01–50% (w/w) with respect to the total weight, varying depending on the kinds of the ingredients used and the fields and forms of the body-odor inhibitory agent used.

Examples of the thickening agents usable in the present invention include, in addition to the ingredients with thickening action among the aforesaid ingredients, water-soluble high-molecular substances such as guar gum, quince seed, tragacanth gum, pectin, xanthan gum, chitin, chondroitin sulfate, dextran sulfate, sodium alginate, cationic cellulose, hydroxyethyl cellulose, carboxymethyl cellulose, carboxymethyl starch, propylene glycol alginate, collagen, keratin, casein, albumin, gelatin, hydroxypropyl trimethylammoniumchloride ether, poly(vinyl alcohol), poly(vinylpyrrolidone), sodium polyacrylate, poly(vinyl methyl ether), carboxy methyl polymer, electrolytes such as sodium chloride, potassium chloride, and sodium sulfate, and oil components. The use of these thickening agents improve or control the application feeling when the body-odor inhibitory agent of the present invention is used by directly applying to the skin. The content of these ingredients preferably used in the body-odor inhibitory agent of the present invention is usually 0.01–30% (w/w) with respect to the total weight, varying depending on the kinds of the ingredients used and the fields and forms of the body-odor inhibitory agent used.

The above carboxyvinylpolymer such as commercially available "CARBOPOL", carboxypolymethylene, product Nos. 934, 940, 941, etc., produced by B. F. Goodrich Chemical, USA, can be particularly advantageously used to provide the body-odor inhibitory agent in a gel form of the present invention because such carboxyvinylpolymer has an action of gelling solutions when used in combination with alkaline ingredients, and the resulting gels formed by carboxyvinylpolymer far less change in viscosity susceptible to temperature than other thickening agents. Examples of such carboxyvinylpolymer are inorganic bases such as those of sodium hydroxide, potassium hydroxide, and ammonium hydroxide; and organic bases such as those of triethanolamine and L-arginine. The content of carboxyvinylpolymer preferably used in the body-odor inhibitory agent in a gel form of the present invention is usually 0.1–10% (w/w) with respect to the total weight, and the alkaline ingredients are used in an amount sufficient to neutralize carboxyvinylpolymer, usually, in an amount that can adjust the pH of the body-odor inhibitory agent to a pH of around 6–7.5.

The term "powdered materials" as referred to in the present invention means powdery ingredients which are substantially incapable of dissolving in water or organic solvents and are usually permitted for use in the field of skin external applications. Examples of such powdered materials include, in addition to those which fulfil the definition among the aforesaid ingredients, synthetic resin powders such as a nylon or polyamide powder, polyurethane powder, polyethylene powder, polystyrene powder, cross-linked polystyrene powder, and cross-linked silicon powder; powders of white, red, brown, yellow, black, purple, green or blue inorganic-pigments including silicic acid anhydride, magnesium oxide, magnesia silica or a composition containing silicic acid anhydride and magnesium oxide, montmorillonite, hydroxyapatite, magnesium silicate, mica, carbon black, sericite, zeolite, aluminum oxide, zirconium oxide, calcium carbonate, magnesium carbonate, barium sulfate, mica titanium or a powdered mica coated with a thin membrane of titanium oxide, calcium oxide, ballium silicate, calcium silicate, and powdered pearl; powders of organic pigments; powders of metal pigments; and natural powders such as silk- and wool-powders. These powdered materials can be used in the body-odor inhibitory agent of the present invention as coloring agents, bases, excipients, carriers, coatings, and gloss-imparting agents. The content of these ingredients preferably used in the body-odor inhibitory agent of the present invention is usually 0.01–50% (w/w) with respect to the total weight, varying depending on the kinds of the ingredients used and the fields and forms of the body-odor inhibitory agent used.

Examples of the refreshing agents usable in the body-odor inhibitory agent of the present invention include menthol, camphor, peppermint oil, peppermint oil, cinnamon oil, fennel oil, bergamot oil, and d-borneol. The content of these ingredients preferably used in the body-odor inhibitory agent of the present invention is usually 0.001–5% (w/w), and preferably 0.01–1% (w/w) with respect to the total weight, varying depending on the kinds of the ingredients used and the fields and forms of the body-odor inhibitory agent used. When used in the present invention the above-mentioned ingredients other than trehalose and maltitol, and other ingredients such as squirt agents, pH-controlling agents, flavors, deodorants, colors, proteins, amino acids, fibers, lipids, and salts, they should preferably be the preparations acceptable for use in respective fields of the body-odor inhibitory agent of the present invention to used; it is no use saying that the preparations acceptable for external or internal use for living bodies are desirably used when the body-odor inhibitory agent is used by contacting with the living bodies directly or indirectly.

Depending on purposes, the incorporation of appropriate ingredients selected from the above ingredients other than trehalose and/or maltitol into the body-odor inhibitory agent of the present invention imparts the desired properties and functions to the body-odor inhibitory agent. For example, as an example, the body-odor inhibitory agent of the present invention, which comprises trehalose and/or maltitol, water and/or alcohol as a solvent, antiperspirant, germicide, feeling improver, and powdered material, characteristically exerts a remarkable body-odor inhibitory effect, inhibits the perspiration similarly as commercialized antiperspirant or deodorant products, and makes user feel refresh when administered to the skin of living bodies.

Depending on the fields and forms used, the body-odor inhibitory agent of the present invention thus constructed can be prepared into those in the form of liquids such as aqueous solutions, lotions, spray liquids, suspensions or emulsions; solids such as powders, granules, and blocks; and semisolids and gels such as creams or pastes; and if necessary the resulting mixtures can be injected into appropriate vessels such as bottles, bags, cans, spraying cans, spraying vessels, casements, and packs. When used according to the later described method for inhibiting body-odor according to the present invention, the aforesaid body-odor inhibitory agent of the present invention inhibits the formation of body odor of humans and animals other than humans such as mammals, poultry, and fishery. Examples of such animals are the following pet- and enjoyment-animals and livestocks: Predatory animals including dogs, cats, foxes, and raccoon dogs; rodents such as squirrels, hamsters, mice, guinea pigs, and rabbits; primates excluding humans such as lemurs, aye-aye, tarsiers, and long-armed apes; artiodactyl animals such as cows, sheep, goats, wild boars, and pigs; perissodactyl animals. such as horses, which are all mammals; poultry including domestic fowls, turkeys, bantams, quails, parakeets, Java sparrows, canaries, society finches, hill mynas, and pigeons; and fishery such as tropical fishes, goldfishes, carp, sea breams, shrimps, and crabs. Thus, the body-odor inhibitory agent of the present invention can be advantageously used daily by everyone and also used, for example, in the industries of barbershops and beauty parlors, public bathhouses including hot springs, esthetics, massages, cleanings, livestocks and fishery, fields of handling pets and animals for enjoyment such as mammals, poultry and fishery, as well as in the fields of medicals and cares/carings/nursing cares.

The body-odor inhibitory agent of the present invention in itself is useful to inhibit body odor and can be advantageously used in the form of articles which can be contacted with living bodies. The term "articles which can be contacted with living bodies" means those which can be used by contacting with the living bodies of humans and animals directly or indirectly. Examples of the articles are woven fabrics, non-woven fabrics, sponges, macroporous synthetic resins, cottons, and absorbent cottons, which are formed into the form that can be used in the field of cosmetics, daily goods, hygienic goods, goods for medical use, goods for care/caring/nursing care, and sport goods. Particular examples of respective articles which can be used by incorporating the body-odor inhibitory agent of the present invention are daily goods such as tissue papers, wet tissue papers, towels including wet paper-towels, wet towels, hand towels, and foot towels, handkerchiefs, cushions, and door covers; laundry goods such as laundry detergents, laundry finishings, softeners, and starching agents for washing clothes, bedclothes, and daily goods; clothes including disposals formed with papers such as those in the form of underwears, socks, anklets, stockings, shirts, trousers, and skirts; bed clothes such as sheets, thick bedquilt covers, blankets including pillow blankets, and towelkets; personal items such as globes, caps, hats, mufflers, headbands, hair bands, and shoes; hygienic goods such as bandages, eye bandages, gauzes, sticking plasters with pads, wet compresses, basal cloths of wet compresses, swabs, masks, diapers including disposal ones, and sanitary goods such as menstrual sanitary; goods for medical use and for care/caring/nursing care; sport goods such as sport shoes, training wears, supporters, singlets, helmet pads, gloves, and mitts; cleaning goods such as floorcloths, dishcloths, and mops; lotions, creams and gels for esthetics, massages, care goods for body odor; external dermatological compositions such as nursery powders; compositions for scalp and hair use such as shampoos, dry shampoos, rinses, hair tonics, hair liquids, hair mousses, hair creams, pomades, hair-restorers, hair tonics, and hair restorers; compositions for oral use such as mouth washes and toothpastes; and articles for pet animals such as feeds for fishery, detergents for aquariums, and bath salts for pet animals. Varying depending on the forms and uses, the above articles incorporated with the body-odor inhibitory agent of the present invention usually contain trehalose and/or maltitol in a total weight of about 0.00001% to about 30%, and preferably about 0.0001% to about 10%, d.s.b. When used similarly as in conventional articles which do not contain the present body-odor inhibitory agent, the above articles effectively inhibit the formation of body odor from living bodies to be applied, and effectively inhibit body odor or the likes which are induced by the secretion from the living bodies. As described in detail in the below, since the body-odor inhibitory agent of the present invention effectively inhibits the formation of 2-nonenal, 2-octenal and 2-hexenal which are known as substances causative of KAREI-SHU, the aforesaid articles can be advantageously used as for inhibiting KAREI-SHU.

The present invention provides a method for inhibiting body odor, characterized in that it comprises a step of contacting the above-mentioned body-odor inhibitory agent with the secretion from living bodies. Examples of the secretion form living bodies include sebums and sweat. The method according to the present invention is not specifically restricted to particular ones with respect to means for contacting and the dose of the body-odor inhibitory agent as long as it can inhibit body odor by contacting the agent with the secretion from living bodies at the stage of forming body odor. For example, the following is an example of the method of the present invention, i.e., contacting directly the body-odor inhibitory agent with fishery for enjoyment or with appropriate parts on the surface of living bodies such as skins and hairs of humans and other animals. To inhibit body odor by directly applying the body-odor inhibitory agent of the present invention to living bodies, for example, it can be effected by allowing the agent in an appropriate form such as a liquid, cream, or paste, which comprises water and/or alcohols as solvents and trehalose and/or maltitol usually in a total weight of about 0.0001% to about 20%, and preferably about 0.001% to about 5% by weight, with respect to their anhydrous forms.

The method for inhibiting body-odor according to the present invention can be advantageously carried out by sequentially incorporating the agent into articles to be contacted with living bodies, and contacting the agent with the secretion from the living bodies. The articles for which the body-odor inhibitory agent can be advantageously applied include any of the above-exemplified articles. To contact the body-odor inhibitory agent with the secretion from living bodies after the agent is incorporated into the articles, for example, it can be effected by either spraying to the whole or appropriate parts of the articles to be treated an adequate amount of the body-odor inhibitory agent in the form of a liquid or spray, which comprises water and/or alcohol(s) as solvents and trehalose and/or maltitol in a total weight of about 0.0001% to about 10%, and preferably about 0.001% to about 1% by weight, with respect to their anhydrous forms; or soaking the articles in the liquid; and then, if necessary, drying the resulting articles prior to usual use. As the merit, in the case of using, in a conventional manner, articles including daily goods, clothes, and bedclothes, which are incorporated or washed with the body-odor inhibitory agent in a conventional manner, the body-odor inhibitory agent effectively inhibits the body-odor of living bodies to be contacted with the articles, and well inhibits the pollution or the adhesion of undesirable daily-occurring odors other than body odor such as smells of tobaccos, grilled fish and meat, and Chinese noodles.

The method for inhibiting body-odor according to the present invention can be also advantageously effected by incorporating the body-odor inhibitory agent into water which may be contacted with living bodies, and then contacting the agent with the secretion from living bodies. The term "water which can be contacted with living bodies" means water which may contain lipid(s) and can be contacted with living bodies; water in pools for competitive swimming and playing, bath water of bathhouses, and water in aquariums for pet and ornamental animals; and water in aquariums for ornamental fishery. After incorporating the body-odor inhibitory agent into water, the agent can be preferably with the secretion from living bodies, for example, by incorporating trehalose and/or maltitol into water, usually, in a total concentration of about 0.00001% to about 5% by weight, and preferably in an amount of about 0.0001% to about 1% by weight, with respect to their anhydrous forms, prior to use.

The use of the method for inhibiting body-odor according to the present invention inhibits the formation of body odor or the likes from articles and waters to be treated, and body odor from living bodies per se, which had been contacted with the body-odor inhibitory agent, and articles or water containing the agent, for example, smells of sweat, armpit, foot, dandruff, KAREI-SHU, and mouth. Particularly, the body-odor inhibitory agent of the present invention effectively inhibits the formation of volatile aldehydes as ingredients of body odor, and particularly saturated volatile aldehydes such as propanal, butanal, pentanal, hexanal, heptanal, octanal, nonanal, and decanal; and unsaturated volatile aldehydes such as 2-nonenal, 2-octenal, and 2-hexenal. Among these volatile aldehydes, unsaturated volatile ones are known as the main substances causative of KAREI-SHU so that the method of the present invention is also useful as a method for inhibiting KAREI-SHU. The method for inhibiting body-odor of the present invention can be advantageously used in the diversified fields that handle articles and water in which the formation of body odor of humans and animals should preferably be inhibited. Examples of the fields that handle water are manufacturers to clean clothes and bedclothes, rental services for bedclothes such as sheets, quilts and beddings, costumiers of uniforms and formal dresses, costumiers of daily goods such as towels, wet towels, foot towels, costumiers to clean goods such as floorcloths and mops for home and business uses, and costumiers of goods for care/caring/nursing care such as diapers. Examples of the fields that handle water are athletic gymnasiums equipped with bathhouses, hot springs, or whirling hot tabs. Examples of the fields, that handle articles and water in which body odor from animals other than humans should preferably be inhibited, are raising and sale of aquarium fish and fishery such as goldfishes, zoos equipped with bathing facilities for animals, and aquariums equipped with water tanks for fishery.

Explaining the present invention with reference the following Experiments; in Experiments 1 to 5, there is provided an acceleration test system for forming body-odor where fatty acids were heated to form volatile aldehydes known as the main substances causative of body odor; and in Experiment 6, there is provided a test system of body-odor formation for forming volatile aldehydes by keeping fatty acids at the temperature of human body to examine the influence of the addition of saccharides on the test system. While in Experiments 7 and 8, the influence of saccharides on the formation of body odor from living bodies was examined using volunteers.

Experiment 1
Influence of Saccharides on the Formation of Volatile Aldehydes from Oleic Acid by Heating One hundred milligrams of oleic acid as a fatty acid, 500 mg of cellulose powder, and 1.25 ml of 0.12 M phosphate buffer (pH 6.0) were placed in a 20-ml glass vial. To the glass vial were added 100 mg of either of crystalline trehalose hydrate, crystalline maltitol anhydride, crystalline sorbitol anhydride, crystalline sucrose anhydride, crystalline maltose anhydride, and crystalline neotrehalose hydride as test saccharides (throughout Experiments 1 to 6, these saccharides are designated as "trehalose", "maltitol", "sorbitol", "sucrose", "maltose", and "neotrehalose", respectively), followed by sealing the glass vial with a butyl rubber. As a control system, there provided a glass vial, with no a test saccharide, which differed from the test glass vial on this point. These glass vials were heated at 105° C. for one hour, cooled to ambient temperature, and kept in an aluminum heat-block (abbreviated as "heat block, hereinafter"), which had been preheated to 80° C. After 5-minutes standing, two milliliters of a head space gas (abbreviated as "HSG", hereinafter) were collected from each glass vial with a syringe.

The collected HSG was analyzed for content of volatile aldehydes on gas chromatography (abbreviated as "GC" hereinafter) using "GAS CHROMATOGRAPH GC-14A", as a GC apparatus; "CAPILLARY COLUMN SUPELCO-WAX", having 0.25 mm in inner diameter, 60 m in length, and 0.25 μm in thickness, commercialized by Supelco Inc., Tokyo, Japan, as a column for analysis; helium gas at a flow rate of one ml/min as a carrier gas, under temperature conditions of 250° C. for injecting a sample and of a column thermostatic bath temperature being kept at 80° C. for five minutes and then increased up to 240° C. at a rate of 5° C./min. As standard specimens, propanal, butanal, and hexanal as volatile aldehydes were used. Based on the peak area obtained from gas chromatography for the standard specimens and HSG samples, the content of respective volatile aldehydes in HSG was calculated.

Upon the HSG samples, the level of a body-odor-like smell was examined on a panel test consisting of six professional panels; the panels directly smelled the samples from each glass vial and judged the level of the smells for each samples with test saccharides based on the following four ranks, i.e., the same or higher level of odor (+++), slightly lower level of odor (++), clearly lower level of odor (+), and odorless (−) as compared with the control system. Summing up the data from the panels, the samples tested were totally evaluated.

Table 1 shows the results of the panel test and the data of HSG samples on GC analysis.

TABLE 1

| Test saccharide | Content in HSG (μg/ml) | | | Evaluation of panel test* |
|---|---|---|---|---|
| | Propanal | Butanal | Hexanal | |
| Non (control system) | 9.41 | 1.04 | 0.08 | +++ |
| Trehalose | 3.47 | 0.19 | 0.02 | + |
| Maltitol | 4.09 | 1.02 | 0.03 | ++ |
| Sorbitol | 8.31 | 1.06 | 0.06 | +++ |
| Sucrose | 9.98 | 1.11 | 0.07 | +++ |
| Maltose | 9.09 | 1.38 | 0.07 | +++ |
| Neotrehalose | 8.89 | 1.25 | 0.08 | +++ |

Note:
In the column of evaluation of panel test*, the symbols "+++", "++", and "+" mean that it smells the same or higher level of odor, slightly lower level of odor, and clearly lower level of odor than that of the control system, respectively.

As evident from the results in Table 1, the system with trehalose or maltitol, particularly, the one with trehalose was low in the total amount of volatile aldehydes formed in HSG by heating oleic acid, as compared with the control system. Referring to each ingredient, the formation level of hexanal known as the main body-odor of humans and animals was particularly low in the systems with trehalose and maltitol. As shown in the result from the panel test, both systems with trehalose and maltitol effectively inhibited the formation of a body-odor-like smell than other systems.

Experiment 2
Influence of Saccharides on the Formation of 2-nonenal from Linoleic Acid by Heating The content of 2-nonenal in HSG was measured by GC similarly as in Experiment 1 except that linoleic acid was used as a fatty acid and 2-nonenal, a volatile aldehyde, was used as a standard substance. The level of a body-odor-like smell, particularly with respect to KAREI-SHU, in each sample was evaluated by panel test in accordance with the method in Experiment 1.

The results from the GC analysis of HSG and the panel test are tabulated and shown in Table 2.

TABLE 2

| Test saccharide | Content of 2-nonenal in HSG (μg/ml) | Evaluation of panel test* |
|---|---|---|
| Non (control system) | 5.75 | +++ |
| Trehalose | 1.27 | + |
| Maltitol | 1.73 | + |
| Sorbitol | 5.12 | +++ |
| Sucrose | 5.41 | +++ |
| Maltose | 4.60 | +++ |
| Neotrehalose | 5.64 | +++ |

Note:
In the column of evaluation of panel test*, the symbols "+++", "++" and "+" mean that it smells the same or higher level of odor, slightly lower level of odor, and clearly lower level of odor than that of the control system, respectively.

As shown in Table 2, the system with trehalose or maltitol, particularly, the one with trehalose was clearly low in the content of 2-nonenal formed in HSG by heating linoleic acid. As found in the result from the panel test, the formation of a body-odor-like smell including KAREI-SHU was more inhibited in both the systems with trehalose and maltitol than other systems.

Experiment 3
Influence of Saccharides on the Formation of 2-nonenal from 9-hexadecanoic Acid by Heating The content of 2-nonenal in HSG was measured by GC similarly as in Experiment 1 except that 9-hexadecanoic acid or palmitoleic acid was used as a fatty acid and 2-nonenal, a volatile aldehyde, was used as a standard substance. The level of body-odor-like smell, particularly with respect to KAREI-SHU, in each sample was evaluated by panel test in accordance with the method in Experiment 1.

The results from the GC analysis of HSG and the panel test are tabulated and shown in Table 3.

TABLE 3

| Test saccharide | Content of 2-nonenal in HSG ($\mu$g/ml) | Evaluation of panel test* |
|---|---|---|
| Non (control) | 25.7 | +++ |
| Trehalose | 4.10 | + |
| Maltitol | 6.17 | + |
| Sorbitol | 23.6 | +++ |
| Sucrose | 24.4 | +++ |
| Maltose | 24.2 | +++ |
| Neotrehalose | 25.7 | +++ |

Note:
In the column of evaluation of panel test*, the symbols "+++", "++" and "+" mean that it smells the same or higher level of odor, slightly lower level of odor, and clearly lower level of odor than the control system, respectively.

As shown in Table 3, the system with trehalose or maltitol, particularly, the one with trehalose was clearly low in the content of 2-nonenal formed in HSG by heating 9-hexadecanoic acid. As found in the result in the panel test, the formation of body-odor-like smell including KAREI-SHU was more inhibited in both the systems with trehalose and maltitol than other systems.

Experiment 4
Influence of Saccharides on the Dispersion of 2-nonenal

Ten milligrams of 2-nonenal, 500 mg of a cellulose powder, and 1.25 ml of 0.12 M phosphate buffer (pH 6.0) were placed in a 20-ml glass vial. To the glass vial was added 100 mg of either of trehalose, maltitol and sucrose as a test saccharide, followed by sealing with a butyl rubber cap. As a control system, there provided a glass vial with no test saccharide that differed from the test systems only in this point. These glass vials were kept in a heat block, preheated to 80° C. After 5-min standing, the glass vials were sampled by two milliliters of HSG with a gas syringe. The content of 2-nonenal in the sampled HSG was measured by GC in accordance with the method in Experiment 2. The results are in Table 4.

TABLE 4

| Test saccharide | Content of 2-nonenal in HSG ($\mu$g/ml) |
|---|---|
| Non (control system) | 8.67 |
| Trehalose | 8.60 |
| Maltitol | 8.27 |
| Sucrose | 8.70 |

As shown in Table 4, all the systems with the test saccharides showed substantially the same level of 2-nonenal in HSG as that of the control system. The data suggests that the inhibitory effect of trehalose and maltitol on the formation of 2-nonenal from linoleic acid or 9-hexadecanoic acid, which was confirmed in Experiments 2 and 3, is exerted by their inhibitory effects on the formation of 2-nonenal per se and not by their dispersion inhibitory effects on 2-nonenal.

Experiment 5
Influence of Saccharides on the Decomposition of Fatty Acids by Heating One hundred milligrams of linoleic acid or 9-hexadecanoic acid as a fatty acid, 500 mg of a cellulose powder, and 1.25 ml of 0.12 M phosphate buffer (pH 6.0) were placed in a 20-ml glass vial. To the glass vial was added 100 mg of either of trehalose, maltitol and sucrose as a test saccharide, followed by sealing with a butyl rubber cap. As a control system, there provided a glass vial with no test saccharide that differed from the test systems only in this point. These vials were heated at 105° C. for one hour. Another glass vial with no heat treatment, which contained the same ingredients as shown in the above, was provided that differed from the test systems only in that it had no heat treatment.

The above test systems with or without heat treatment and the control system were subjected to the following methyl esterification reaction and analyzed on GC to measure the content of fatty acids; To each glass vial was added 20 ml of a mixture solution of chloroform and methanol (=2:1 by volume) to extract fatty acids, and one milliliter of each resulting extract was collected in a 10-ml eggplant-shape flask, concentrated, and dried in vacuo. The resulting dried substance in each flask was dissolved by the addition of one milliliter of methanol solution containing 30 mg/ml of tricosanoic acid as an internal standard substance and redried by concentrating in vacuo. After added to each flask one milliliter of boron trifluoride in methanol, the flasks were sealed and kept in a boiling water bath for five minutes for methyl esterification reaction of fatty acids. The reaction mixtures were cooled, admixed with one milliliter of deionized water per flask to decompose the remaining intact boron trifluoride. To each flask was added one milliliter of n-hexane to extract the formed fatty acid methyl ester compounds in a n-hexane layer.

Two microliters of each of the resulting n-hexane layers were analyzed on GC using "GAS CHROMATOGRAPH GC-14A", a GC apparatus, commercialized by Shimadzu Corporation, Tokyo, Japan; and "CAPILLARY COLUMN FFAP", an analysis column having an inner diameter of 0.25 mm, a length of 30 m, and a membrane thickness of 0.25 $\mu$m, commercialized by GL Sciences Inc., Tokyo, Japan, under the conditions of using helium gas as a carrier at a flow rate of 1 ml/min, at a temperature of 250° C. as a sample injection temperature, a column thermostatic bath temperature being kept at 80° C. for five minutes and then increased up to 240° C. at a rate of 5° C./min, and a hydrogen flame ionization detector for detecting fatty acids. Based on the peak area of the obtained gas chromatograms, it was calculated the content of fatty acids, i.e., linoleic acid and 9-hexadecanoic acid, before or after the heat treatment in the test- and control-systems.

The measured values obtained by GC analysis were substituted for the following equation 1 for calculating the decomposition percentage (%) of fatty acids in each system. The results are in Table 5.

Equation 1:

$$\text{Decomposition percentage (\%)} = \frac{A - B}{A} \times 100$$

A: Fatty acid content with no heat treatment

B: Fatty acid content with heat treatment

TABLE 5

| Test saccharide | Decomposition percentage (%) | |
|---|---|---|
| | Linoleic acid | 9-Hexadecanoic acid |
| Non (control system) | 60.0 | 38.1 |
| Trehalose | 25.2 | 13.2 |
| Maltitol | 33.4 | 14.7 |
| Sucrose | 58.0 | 38.5 |

As shown in Table 5, the decomposition percentage of fatty acids by heat treatment in the system with sucrose was substantially the same as that in the control system, while the decomposition percentage in the systems with trehalose and maltitol, particularly that in the system with trehalose was more inhibited than that in the control system. The data revealed that trehalose and maltitol well inhibit the decomposition of fatty acids and evidenced the fact that trehalose and maltitol effectively inhibit the formation of volatile aldehydes, as ingredients of body odor, per se.

Experiment 6
Influence of Saccharides on the Formation of 2-nonenal from 9-hexadecanoic Acid at the Temperature of Human Body One hundred milligrams of 9-hexadecanoic acid as a fatty acid, 500 mg of a cellulose powder, and 1.25 ml of 0.12 M phosphate buffer (pH 6.0) were placed in a 20-ml glass vial. To the glass vial was added 100 mg of either of trehalose, maltitol and sucrose as a test saccharide, followed by sealing with a butyl rubber cap for use as a test system. As a control system, there provided a glass vial with no test saccharide that differed from the test systems only in this point. In both the test- and control-systems, they were respectively provided in doublet.

These glass vials were allowed to stand in a 37° C.-thermostatic-bath under the irradiation of 9,000 lux by a fluorescent lamp. At 3-days of standing, one of each pair of the vials containing the same composition, and 7-days of standing, the other vial of each resting pair of the vials were transferred to a heat block, which had been preheated to 80° C. and then kept therein for five minutes, followed by analyzing the content of 2-nonenal in HSG in each vial by GC similarly as in Experiment 2. After the collection of HSG, the smell from glass vials was evaluated by panel test in accordance with the method in Experiment 2.

The results of the GC analysis of HSG and the panel test are tabulated and shown in Table 6.

TABLE 6

| Test saccharide | Test period | Content of 2-nonenal in HSG (µg/ml) | Evaluation of panel test* |
|---|---|---|---|
| Non (control system) | 3-days | 0.03 | +++ |
| Trehalose | of | 0.00 | − |
| Maltitol | standing | 0.00 | − |
| Sucrose | | 0.26 | ++ |

TABLE 6-continued

| Test saccharide | Test period | Content of 2-nonenal in HSG (µg/ml) | Evaluation of panel test* |
|---|---|---|---|
| Non (control system) | 7-days | 16.8 | +++ |
| Trehalose | of | 2.64 | + |
| Maltitol | standing | 2.77 | + |
| Sucrose | | 16.4 | +++ |

Note:
In the column of evaluation of panel test*, the symbols "+++", "++", "+" and "−" mean that it smells the same or higher level of odor, slightly lower level of odor, clearly lower level of odor than that of the control system, and odorless, respectively.

As shown in Table 6, the formation level of 2-nonenal from 9-hexadecanoic acid at 37° C. in the system with sucrose showed substantially no difference as compared with the control system, while that in the systems with trehalose and maltitol, particularly the one with trehalose was distinctively inhibited as compared with the control system. The data confirmed that, when with the secretion from living bodies present on the surface or thereabout, trehalose and maltitol distinctively inhibit the formation of components of body odor to effectively inhibit the formation of body odor.

Experiment 7
Test on Volunteers

The influence of saccharides on the formation of body odor from living bodies by applying trehalose to a healthy male volunteer, 57 years old, under the following schedule: After soaking a towel in a 2% (w/w) aqueous trehalose solution, which had been boiled for five minutes and then cooled to about 40° C., at 10:30 a.m. on the day of starting a test, the volunteer as in a test system was allowed to wipe his whole body with the towel squeezed roughly to apply trehalose on the body surface, and made him to spend his daily life as usual after the drying of the applied aqueous trehalose solution. Thereafter, he was made to take a bath at 9 p.m. as usual and allowed to sufficiently wash his whole body including his hair. Just after bathing, a fresh preparation of aqueous trehalose solution was applied on the body surface similarly as above, then after drying the aqueous trehalose solution, he was made to wear an underwear and allowed to spend his daily life. At 5:30 p.m. on the next day after the initiation of the test, his worn underwear was collected, and tested for the presence and the content of volatile aldehydes in the underwear by the following procedures. As a control, on other day, the volunteer was allowed to wear a similar underwear as used in the test system according to the above test system except for replacing the aqueous trehalose solution with water, and then made him to spend his daily life, followed by collecting his underwear and analyzing them by the following procedures similarly as above.

As shown schematically in FIG. 1, an underwear 5 worn by the volunteer in each system was sealed after placed in a sealing vessel 1 immediately after the collection, and the gas in the sealing vessel 1 was pumped by an air pump 3 into a cartridge 4, "Superclean LpDNPH Cartridge", with a lot No. LpDNPH S10L commercialized by Supelco Inc., Tokyo, Japan, to collect volatile aldehydes through a pipe 2 at ambient temperature of about 20° C., while the gas was continuously circulated through the sealed vessel 1 through the pipe 2 for one hour to collect in the cartridge 4 volatile aldehydes, as DNPH (dinitrophenylhydrazine), contained in the underwear 5. Thereafter, the cartridge 4 was removed and received two milliliters of acetonitrile by passing therethrough, followed by collecting an eluate from the cartridge 4. The collected eluate was analyzed on GC as follows.

"GAS CHROMATOGRAPH GC-14B", as a GC apparatus produced by Shimadzu Corporation, Tokyo, Japan; and "TC-Wax CAPILLARY COLUMN", a column for analysis, having 0.53 mm in inner diameter, 25 m in length, and 0.5 $\mu$m in thickness, produced by GL Sciences, Inc., Tokyo, Japan, were used. Helium gas was used as a carrier gas at a flow rate of 1 ml/min, and the temperature for a sample injection part was set to 240° C., while keeping a column thermostatic bath temperature at 50° C. for five minutes and then increasing the temperature up to 200° C. at a rate of 5° C./min. Using two microliters of an analysis sample as an injection volume, 1/30 volume of the injected sample was analyzed (split 1:30) by passing through the column for analysis while controlling the flow rate of the carrier gas at the sample injection part and using a hydrogen flame ionization detector for detection. As standard specimens, DNPH derivatives for each 2-nonenal, 2-octenal, hexanal, and nonanal were used and separately analyzed on GC under the conditions shown above. Based on the gas chromatograms from the above analyses, the content ($\mu$g) of respective 2-nonenal, 2-octenal. hexanal, and nonanal, collected form the underwears in the test system and control, was determined. The results are in Table 7.

TABLE 7

| Application of trehalose on the body surface | Content of volatile aldehydes collected from underwear ($\mu$g) | | | |
| --- | --- | --- | --- | --- |
| | 2-Nonenal | 2-Octenal | Hexanal | Nonanal |
| Yes (test system) | 3.72 | —* | —* | —* |
| No (control system) | 7.05 | 8.61 | 5.39 | 10.93 |

Note:
The symbol "*" means no detection.

As shown in Table 7, all the four volatile aldehydes as ingredients of body odor for analysis were detected in the underwear of the volunteer with no application of trehalose to the body surface. While the underwear of the volunteer with trehalose in the test system, it was confirmed that 2-nonenal as the main substance causative of KAREI-SHU lowered to about 53%, 2-octenal lowered to an undetectable level, and other ingredients of body odor, i.e., hexanal and nonanal also lowered to an undetectable level. These data indicate that trehalose well inhibits the formation of body odor including KAREI-SHU when directly contacted with the body surface. An experiment using maltitol in place of trehalose similar to the above experiment revealed that maltitol well inhibits the formation of body odor similarly as trehalose.

Experiment 8
Test on Volunteer

In accordance with the test on volunteer in Experiment 7, the following experiment was conducted with more volunteers, while focusing particularly on the formation inhibitory effect on KAREI-SHU by trehalose. The number of volunteers used in this experiment was 16 healthy males, ranging from 48 to 75 years old. Cotton-made half-sleeve underwears with substantially the same quality were purchased, washed with only water and dried twice in a cyclic manner for volunteers' use as underwears during the test period. As for towels and gauzes used by volunteers during the test period, those with substantially the same quality were purchased, washed with only water and dried twice in a cyclic manner for use. The initiation day of the test was expressed with day 0, and when the volunteers use body-odor-care-goods such as deodorants and bath salts daily, they were asked to suspend their use two days before the initiation of the test, i.e., day −2.

Until about 10 a.m. on day 0, each volunteer was in a usual manner asked to take a bath to sufficiently wash their bodies including hairs. After bathing, they were sequentially allowed to wipe water drops on the surface of their bodies with towels, allowed to wear the prepared underwears, and allowed to spend their daily life as usual.

At about 5 p.m. on day 1, the underwears worn by the volunteers were collected from them and, as underwears for a control system, subjected to the following analysis.

Until 10 a.m. on day 1, each volunteer was allowed to take a bath similarly as done on day 0. Just after bathing, they were allowed to wipe water drops on their body surfaces with towels, and sprayed by a sprayer over upper half parts of their bodies with a 2% (w/w) aqueous trehalose solution, which had been previously prepared and provided to the volunteers, followed by extending the solution to homogeneity over the upper half parts in such a manner of tapping on the surfaces of the parts with gauzes, which had been previously soaked in a fresh preparation of the same solution as above. By repeating the steps of spraying and extending for several times before natural dryness, trehalose was applied over the surfaces of upper half parts of the volunteers. Thereafter, the volunteers were allowed to wear new underwears prepared previously and to spend their daily life as usual.

Until about 10 a.m. on day 2, each volunteer was allowed to take a bath similarly as done on day 0. Just after bathing, the volunteers were applied with trehalose over the surfaces of their upper half parts similarly as done on day 1, then allowed to wear new underwears prepared previously and spend their daily life as usual.

At about 5 p.m. on day 3, the underwears worn by the volunteers were collected from the volunteers and, as underwears for a control system, subjected to the following analysis.

The underwears collected from the volunteers in the control and test systems were instantly treated by the method in Experiment 7, followed by collecting in a column volatile aldehydes as DNPH derivatives from the underwears. The DNPH derivatives collected in the column were subjected to analysis according to the method in Experiment 7. Using as standard specimens 2-nonenal, 2-octenal, and 2-hexenal, they were separately subjected to GC analysis under the same conditions as above. Based on the gas chromatograms obtained from the above analyses, the contents ($\mu$g) of 2-nonenal, 2-octenal, and 2-hexenal, collected from the underwears in the test and control systems, were respectively determined. Respective data obtained from all the volunteers are in Table 8.

TABLE 8

Content of volatile aldehydes collected from volunteer (µg)

| Volunteer | | With no trehalose application (Control system) | | | | With trehalose application (Test system) | | | |
|---|---|---|---|---|---|---|---|---|---|
| | (age) | 2-Nonenal | 2-Octenal | 2-Hexenal | Total* | Nonenal | 2-Octenal | 2-Hexenal | Total* |
| A | (48) | 0.00 | 0.00 | 0.00 | 0.00 | 0.00 | 0.00 | 0.00 | 0.00 |
| B | (48) | 0.18 | 0.00 | 0.00 | 0.18 | 0.00 | 0.00 | 0.00 | 0.00 |
| C | (50) | 0.60 | 0.67 | 0.00 | 1.27 | 0.00 | 0.11 | 0.00 | 0.11 |
| D | (51) | 0.00 | 1.70 | 0.00 | 1.70 | 0.17 | 0.24 | 0.00 | 0.41 |
| E | (52) | 0.00 | 0.37 | 0.50 | 0.87 | 0.00 | 0.28 | 0.68 | 0.97 |
| F | (53) | 0.28 | 1.40 | 0.00 | 1.67 | 0.00 | 1.04 | 0.00 | 1.04 |
| G | (53) | 0.19 | 0.91 | 0.00 | 1.10 | 0.18 | 0.00 | 0.00 | 0.18 |
| H | (54) | 0.30 | 2.97 | 0.00 | 3.27 | 1.17 | 0.00 | 0.00 | 1.17 |
| I | (56) | 7.33 | 6.98 | 0.00 | 14.31 | 1.66 | 1.82 | 0.00 | 3.48 |
| J | (56) | 0.00 | 1.47 | 1.74 | 3.20 | 1.10 | 0.00 | 0.00 | 1.10 |
| K | (57) | 7.89 | 1.40 | 0.00 | 9.30 | 0.00 | 1.07 | 0.00 | 1.07 |
| L | (58) | 7.45 | 6.25 | 7.26 | 20.96 | 1.41 | 2.59 | 0.95 | 4.96 |
| M | (61) | 2.59 | 0.00 | 6.37 | 8.96 | 0.35 | 1.13 | 0.00 | 1.47 |
| N | (68) | 12.38 | 10.62 | 11.46 | 30.47 | 2.71 | 5.43 | 0.00 | 8.14 |
| O | (74) | 7.49 | 7.23 | 9.82 | 24.54 | 4.65 | 4.24 | 0.00 | 8.89 |
| P | (75) | 7.78 | 6.94 | 6.90 | 21.62 | 4.99 | 4.42 | 4.70 | 14.12 |

Note: In the table, "total*" means a total analysis value of 2-nonenal, 2-octenal and 2-hexenal.

As shown in the data of the control system in Table 8, 2-nonenal, 2-octenal and 2-hexenal, known as substances causative of KAREI-SHU, were particularly detected in the underwears from volunteers age over 56. While as found in the data in the control system, although there appeared individual differences, the formation of the above substances causative of KAREI-SHU was clearly inhibited by the application of trehalose over the volunteers' body surfaces. To evaluate the inhibitory effect of trehalose on the formation of KAREI-SHU for each age-group of the volunteers tested, the above data were grouped into two groups, i.e., a group of eight volunteers age 54 or under and a group of eight volunteers age 56 or over, and subjected to a statistical treatment of Wilcoxon test. The results are in Table 9.

TABLE 9

| | | Content of volatile aldehydes collected from volunteers' underwears (µg, mean ± standard deviation) | |
|---|---|---|---|
| Group of volunteers | Ingredients analyzed | With no trehalose application (Control system) | With trehalose application (Test system) |
| Age 54 or under (n = 8) | 2-Nonenal | 0.19 ± 0.21 | 0.19 ± 0.40 |
| | 2-Octenal | 1.00 ± 1.00 | 0.21 ± 0.36[a] |
| | 2-Hexenal | 0.06 ± 0.18 | 0.09 ± 0.24 |
| | Total* | 1.26 ± 1.02 | 0.48 ± 0.50[a] |
| Age 56 or higher (n = 8) | 2-Nonenal | 6.61 ± 3.75 | 2.11 ± 1.87[a] |
| | 2-Octenal | 5.51 ± 3.71 | 2.59 ± 1.92[a] |
| | 2-Hexenal | 5.44 ± 4.39 | 0.71 ± 1.65[a] |
| | Total* | 17.17 ± 10.14 | 5.40 ± 4.66[b] |

Note:
In the table, "total*" means a total analysis value of 2-nonenal, 2-octenal and 2-hexenal. The symbol "a" means that it has a significant statistical difference ($p < 0.05$) to control, and the symbol "b" means that it has a significant statistical difference ($p < 0.01$) to control.

As shown in Table 9, when directed to the volunteers of a group age 56 or over, who form more distinguishably substances causative of KAREI-SHU, in this experiment, trehalose clearly inhibited the formation of such substances. These results of this experiment indicate that the inhibitory effect of trehalose on the formation of KAREI-SHU is more particularly exerted when trehalose is applied to older ages who distinctively form KAREI-SHU.

The following Examples explain the present invention in more detail but should not limit the present invention.

EXAMPLE 1

Body-odor Inhibitory Agent

To 68 parts by weight of isopropanol were added and dissolved therein 30 parts by weight of purified water, 0.9 part by weight of "Cosmetic Grade Trehalose", a crystalline trehalose hydrate powder commercialized by Hayashibara Shoji, Inc., Okayama, Japan, called only "trehalose" throughout the Examples below; 0.9 part by weight of "Powdered MABIT®", a crystalline maltitol anhydride powder commercialized by Hayashibara Shoji, Inc., Okayama, Japan, called only "maltitol" throughout the Examples below; 0.2 part by weight of benzoic acid, and an adequate amount of a flavor. Forty milliliters of the resulting solution and 60 ml of a liquefied carbonated gas as a propellant gas were injected into a 100-ml spraying can to obtain a spray-type body-odor inhibitory agent of the present invention.

The product can effectively inhibit the formation of body odor from living bodies of humans and animals, as well as articles, that are used by contacting with the living bodies, for example, clothes and daily goods in such a manner of spraying directly to particular parts of the living bodies susceptible to form body odor or by spraying to the articles.

EXAMPLE 2

Body-odor Inhibitory Agent

Ninety-eight parts by weight of a 65% (v/v) aqueous ethyl alcohol solution, two parts by weight of trehalose, 0.2 part by weight of maltitol, and an adequate amount of a flavor were mixed and dissolved. The resulting solution was injected into a 100-ml hand sprayer to obtain a spray-type body-odor inhibitory agent of the present invention.

The product can effectively inhibit the formation of body odor from living bodies of humans and animals, as well as articles, that are used by contacting with the living bodies, for example, clothes and daily goods in such a manner of spraying directly to particular parts of the living bodies susceptible to form body odor or by spraying to the articles. Since the product exerts such a satisfactory body-odor inhibitory affect and contains a flavor, it can be also used as an aromatic which perfumes a satisfactorily stabilized and durable aroma.

EXAMPLE 3

Body-odor Inhibitory Agent

Two parts by weight of trehalose, 65 parts by weight of ethanol, and 0.005 part by weight of "photosensitizer 201" were dissolved in water into a total volume of 100 parts by weight of a solution. The resulting solution was injected into a 100-ml hand sprayer to obtain a spray-type body-odor inhibitory agent of the present invention.

The product can effectively inhibit the formation of body odor from living bodies of humans and animals, as well as articles, that are used by contacting with the living bodies, for example, clothes and daily goods in such a manner of spraying directly to particular parts of the living bodies susceptible to form body odor or by spraying to the articles. Since the product contains "photosensitizer 201" having melanin-formation inhibitory action and hearing action on acne, it has also functions of maintaining the cleanness and healthy conditions of the skin.

EXAMPLE 4

Body-odor Inhibitory Agent

Two parts by weight of trehalose, 65 pars by weight of ethanol, 0.2 pat by wight of benzalkonium chloride, 0.04 part by weight of chamomile extract, and 0.2 part by weight of dl-α-tocopheryl acetate were dissolved in purified water, sufficient to give a total amount of 100 parts by weight, to obtain a liquid-type body-odor inhibitory agent of the present invention.

The product satisfactorily inhibits the formation of body odor from parts anxious about the formation of human body odor by applying directly to the parts, and inhibits the formation of body odor from the surfaces of living bodies and appropriate parts such as scalps and hairs by incorporating in appropriate articles such as woven fabrics and non-woven fabrics, and then wiping with the resulting articles the surfaces and appropriate parts of the living bodies. Since the product exerts satisfactory anti-inflammatory- and antiseptic-actions, it also has a function of maintaining the health conditions of the skin.

EXAMPLE 5

Body-odor Inhibitory Agent

To 2.0 parts by weight of trehalose, 0.1 part by weight of dipotassium glycyrrhizinate, 1.0 part by weight of sage extract, 0.2 part by weight of sodium citrate, and 0.05 part by weight of p-oxymethyl benzoate was added and dissolved in purified water sufficient to give a total amount of 100 parts by weight into a liquid-type body-odor inhibitory agent of the present invention.

When used by applying to the parts anxious about the formation of human body-odor, the product well inhibits the formation of body odor from the parts. Since the product exerts satisfactory anti-inflammatory- and antiseptic-actions, it also has a function of maintaining the health conditions of the skin.

EXAMPLE 6

Body-odor Inhibitory Agent

Sixty parts by weight of dried sodium sulfate, 30 parts by weight of sodium bicarbonate, 5 parts by weight of trehalose, 4.5 parts by weight of maltitol, one part by weight of a citrus seasoned flavor, and 0.5 part by weight of FD & C Blue No. 2 (C.I. 73015), were mixed to homogeneity into a body-odor inhibitory agent of the present invention.

In use, about 20 g of the product is added to and dissolved in 100 l hot-bath-water. The product effectively inhibits the formation of human body-odor in bath, inherent to the secretion in the water from living bodies, after bathing. The product can be also satisfactorily used as a body-odor inhibitory agent for animals such as pets.

EXAMPLE 7

Hair Tonic 0.03 part by weight of trehalose, 0.005 part by weight of "photosensitizer 301", 0.01 part by weight of rutin glucoside, and 45 parts by weight of anhydrous ethanol were dissolved in purified water to give a total amount of 100 parts by weight. The resulting solution was injected to a 100-ml vessel to obtain a hair tonic containing the body-odor inhibitory agent of the present invention.

The product exerts satisfactory hair-growth action by "photosensitizer 301" and rutin glucoside. Since "photosensitizer 301" has action of lowering the formation of dandruff, the product contains trehalose as the body-odor inhibitory agent of the present invention, and effectively exerts the formation of body odor from scalps with a dandruff smell. Thus, the product is a hair tonic that maintains the clearness and health conditions of the scalps and hairs.

EXAMPLE 8

Wet Tissue

In a mixture solution consisting of 0.4 part by weight of glycerine and 98 parts by weight of purified water were dissolved 0.5 part by weight of trehalose, 0.5 part by weight of maltitol, 0.4 part by weight of succinic acid, and 0.2 part by weight of "αG RUTIN", α-glucosyl hesperidin commercialized by Toyo Refining Co., Ltd., Tokyo, Japan, to obtain a body-odor inhibitory agent of the present invention. A wet tissue was obtained by soaking an adequate amount of the product in a non-woven fabric made of copper ammonium cellulose fiber.

The product can be used similarly as conventional wet tissues and advantageously used as a daily good for inhibiting body odor because it can inhibit the formation of body odor from the skin of humans and animals when applied thereunto.

EXAMPLE 9

Sizing Asent

An aqueous solution containing 10% by weight of hydroxypropyl starch, 3% by weight of polyethylene glycol, 1% by weight of trehalose, 1% by weight of silicon emulsion, and 10% by weight of isopropyl alcohol was prepared as a sizing agent containing the body-odor inhibitory agent of the present invention.

The product is diluted with water by twofold and used to size clothes such as shirts and bathrobes including informal kimonos, and bedclothes such as sheets. When used by contacting with living bodies such as humans and animals after sizing the above articles, the product inhibits the formation of body odor, inherent to the secretions from the living bodies, from the articles during or after their use. The articles, sized with the product, effectively inhibits the formation of the body odor from living bodies who use the articles.

EXAMPLE 10

Softener

According to conventional manner, ester exchange reaction was applied to N-ethyldiethanolamine and fatty acid methyl ester with a carbon chain length of 18 to obtain a reaction product in an ester exchange percentage of about 95%. A tertiary amine in the reaction product was in a usual manner made into a quaternary form in a percentage of 50% using methyl chloride to obtain a base for softener having an iodine value of about 62.

Thirty parts by weight of the above softener, 20 parts by weight of hexylene glycol, 30 parts by weight of water, 10 parts by weight of trehalose, and 10 parts by weight of maltitol were sufficiently mixed and emulsified into a softener containing the body-odor inhibitory agent of the present invention.

Similarly as in conventional softeners for landry, the product can be used during or after washing articles. When used by contacting with living bodies such as humans and animals, the articles treated with the product effectively inhibits the formation of body odor, inherent to the secretions from living bodies, from the articles during or after their use. The articles treated with the product satisfactorily inhibits the formation of body odor from living bodies.

EXAMPLE 11
Mouth Wash

To 20 parts by weight of ethanol, four parts by weight of trehalose, two parts by weight of maltitol, four parts by weight of sorbitol, 0.1 part by weight of dipotassium glycyrrhizinate, 0.2 part by weight of sodium N-lauroylsarcosinate, 0.08 part by weight of saccharin sodium, 0.1 par by weight of trimethyl glycine, and an adequate amount of a flavor were added to purified water to give a total amount of 100 parts by weight, followed sufficiently mixing and dissolving the contents into a mouth wash containing the body-odor inhibitory agent of the present invention.

When used similarly as conventional mouth washes, the product effectively inhibits the formation of mouth odor and makes you feel refresh in your mouth.

EXAMPLE 12
Fish Feed

Sixty-seven parts by weight of a fish meal, one part by weight of trehalose, one part by weight of maltitol, 0.5 part by weight of a dried brewer's yeast, 0.36 part by weight of inositol, 0.04 part by weight of dl-α-tocopheryl acetate, 0.05 part by weight of one percent by weight of β-carotenoid, one part by weight of calcium lactate, 0.6 part by weight of potassium dihydrogenphosphate, 0.3 part by weight of magnesium sulfate heptahydrate, 0.1 part by weight of salt, and 0.05 part by weight of one percent by weight of L-ascorbic acid-2-glucoside were mixed to homogeneity. To the mixture was added eight parts by weight of water, and the resulting mixture was mixed to homogeneity. The mixture thus obtained was in a usual manner granulated into an about 100 mg fish feed per granule.

Similarly as conventional feeds for fish such as those for enjoyment, the product is added to aquariums in use. In addition to the use as fish feed, the product effectively inhibits the formation of fish body-odor in water of aquariums, induced by the secretions from fish. In the product per se, the formation of an unpleasant fish-like smell, induced by the oxidation of aromatic compounds and fatty acid compounds contained therein, is satisfactorily inhibited during use and storage.

EXAMPLE 13
Method for Inhibiting Body Odor

A shirt, previously washed and dehydrated in a usual manner, was soaked in an aqueous solution prepared by diluting with water by twofold a sizing agent obtained by the method in Example 9, and then pressed to size in a usual manner. As a control, another shirt, which had been previously washed and dehydrated similarly as above, was sized by using another sizing agent free of trehalose, which only differed from the above one on this point.

The shirts sized in this example and the control were worn on the same person at different days. For the shirt of this example, the formation of body odor was well inhibited during and after the wearing. Comparing with the case of wearing the shirt of control, in the case of wearing the shirt of this example, the formation of body odor from living body was lowered during and after the wearing.

The method in this example with such a satisfactory effect can be advantageously applied not only to shirts but to laundry businesses for clothes in general for humans and animals, bedclothes in general, and daily goods in general, as well as rental businesses thereof.

EXAMPLE 14
Method for Inhibiting Body Odor

A used wet-towel was washed in a usual manner and dehydrated after rinsed with an aqueous solution containing 0.2% by weight of trehalose, 0.2% by weight of maltitol, and 250 ppm sodium hypochlorite. As a control, another wet-towel, which had been previously washed similarly as above, was dehydrated after rinsed with another aqueous solution with no trehalose and maltitol, which only differed from the above solution on this point.

The wet-towels obtained in this example and the control were allowed to use by the same person at different days. After standing of the wet-towels used in the above, the formation of a body-odor-like smell from living body was well inhibited in the wet-towel of this example. Comparing with the case of using the wet-towel of control, the formation of body odor from living body was lowered in the case of using the wet-towel of this example. As for damp odor, the wet-towel of this example was clearly lower than that of control. These data indicate that trehalose and maltitol have satisfactory inhibitory effect not only on body odor but unpleasant smells induced by fibers per se and detergents.

The method with such a satisfactory effect of this example can be advantageously applied not only to wet-towels but rental businesses of daily goods such as towels and foot mats for restaurants, barbershops, beauty salons, and saunas, etc.

EXAMPLE 15
Method for Inhibiting Body Odor

A body-odor inhibitory agent obtained by the method in Example 6 was added to and dissolved in hot water in bath in an amount of about 0.01% by weight.

When persons were allowed to take a bath with hot water, the resulting hot water in bath was well inhibited from forming a body-odor-like smell. As compared with the case of bathing in conventional hot water in bath, persons bathed in the hot water in bath in this example less formed body odor from living bodies after bathing.

The method of this example with such a satisfactory effect can be advantageously used in bathhouses, hot springs, and athletic gymnasiums equipped with bathhouses, etc.

As described above, the present invention was made based on the self-findings that trehalose and maltitol effectively inhibit the formation stage of body odor of humans and non-human animals such as mammals, poultry and fishery. Since the trehalose and/or maltitol used in the present invention are the compounds that had been confirmed their safety for skin application, the body-odor inhibitory agent, the method for inhibiting body odor using the agent, and the articles incorporated with the agent can be advantageously used in a variety of fields where the inhibition of body-odor inherent to humans and non-human animals is desired.

The present invention with such an outstanding action and effect is a significant invention that greatly contributes to this art.

While there has been described what is at present considered to be the preferred embodiments of the invention, it will be understood the various modifications may be made therein, and it is intended to cover in the appended claims all such modifications as fall within the true spirits and scope of the invention.

We claim:

1. A composition for inhibiting body odor, which comprises trehalose or trehalose and maltitol as effective ingredients and a carrier, said effective ingredients being present in an amount sufficient to inhibit the formation of one or more ingredients selected from the group consisting of 2-nonenal, 2-octenal, and 2-hexenal as ingredients of body odor.

2. The composition of claim 1, which further contains water and/or alcohol.

3. The composition of claim 1, which further contains one or more members selected from the group consisting of maltooligosaccharides, cyclic saccharides, neutral polysaccharides, humectants, antibacterial agents, bacteriostats, germicides, antiseptics, antioxidants, ultraviolet shielding agents, ultraviolet absorbents, antiperspirants, vitamins, plants extracts, photosensitizers, emulsifiers, surfactants, feeling improvers, thickening agents, powdered materials, and refreshing agents.

4. The composition of claim 1, which is in the form of a liquid, solid, semisolid, or gel.

5. An article which can be contacted with a living body and which contains the composition of claim 1.

6. The article of claim 5, which is a member selected from the group consisting of woven fabrics, non-woven fabrics, sponges, macroporous synthetic resins, cottons, and absorbent cottons.

7. The article of claim 5, which is a member selected from the group consisting of daily goods, landry goods, clothes, bedclothes, personal items, goods for hygiene, medical supplies, goods for care/caring/nursing care, sport goods, cleaning goods, compositions for external application, compositions for scalp and hair, oral compositions, and goods for pets.

8. A method for inhibiting body odor, which comprises a step of contacting said composition of claim 1 with the secretion from a living body.

9. The method of claim 8, which comprises the steps of contacting said composition with an article which can be contacted with said living body, and contacting said composition with the secretion from said living body.

10. The method of claim 9, wherein said article is a member selected form the group consisting of woven fabrics, non-woven fabrics, sponges, macroporous synthetic resins, cottons, and absorbent cottons.

11. The method of claim 9, wherein said article is a member selected from the group consisting of daily goods, laundry goods, cloths, bedclothes, personal items, goods for hygiene, goods for medical use, goods for care/caring/nursing care, sports goods, goods for cleaning, compositions for external application, compositions for scalp and hair, oral compositions, or goods for pets.

12. The method of claim 8, which comprises the steps of incorporating said composition into water which can be contacted with said living body, and contacting said composition with the secretion from said living body.

13. The method of claim 12, wherein said water is hot water for bath.

14. The method of claim 8, wherein the secretion is sweat or sebum.

15. The method of claim 8, wherein the secretion exists on the surface of said living body.

16. An article of clothing, a handkerchief, a sheet, a bed quilt cover, a blanket, a mask, a diaper, a sanitary napkin, a dish cloth or a mop impregnated with the composition of claim 1.

17. A method for inhibiting body odor, which comprises contacting a living body in need of said inhibiting with an article of clothing according to claim 16.

18. A composition for inhibiting body odor, consisting essentially of trehalose or trehalose and maltitol as effective ingredients;

optionally one or more members selected from the group consisting of maltooligosaccharides, cyclic saccharides, neutral polysaccharides, humectants, antibacterial agents, bacteriostats, germicides, antiseptics, antioxidants, ultraviolet shielding agents, ultraviolet absorbents, antiperspirants, vitamin A, thiamine, vitamin C, vitamin E, vitamin P, plants extracts, photosentsitizers, emulsifiers, surfactants, feeling improvers, thickening agents, powdered materials, and refreshing agents; and a carrier.

* * * * *